United States Patent [19]

Suter

[11] Patent Number: 4,783,413
[45] Date of Patent: Nov. 8, 1988

[54] APPARATUS FOR SUPPLYING A MEDIUM TO A REACTION CHAMBER

[75] Inventor: Robert N. Suter, Zurich, Switzerland
[73] Assignee: Contraves AG, Zurich, Switzerland
[21] Appl. No.: 49,436
[22] Filed: May 14, 1987

[30] Foreign Application Priority Data

Jul. 30, 1986 [CH] Switzerland .............. 03058/86

[51] Int. Cl.[4] .................................. C12M 13/00
[52] U.S. Cl. ........................... 435/284; 435/284; 435/287; 604/892.1
[58] Field of Search ............ 435/313, 284, 285, 286, 435/289, 288; 604/892

[56] References Cited

U.S. PATENT DOCUMENTS 3,887,436  6/1975  Haddad et al. ............... 435/285
4,546,086 10/1985  Hounsell ...................... 435/287
4,680,266  7/1987  Tschopp et al. .............. 435/287 X

FOREIGN PATENT DOCUMENTS 580961  9/1976  Switzerland .

OTHER PUBLICATIONS

Pharmacology & Therapeutiks, vol. 21, 6/1983, pp. 35 to 51, Pergamon Press Ltd., Great Britain; Article of Robert Langer, entitled "Implantable Controlled Release Systems".

Primary Examiner—Larry Jones
Attorney, Agent, or Firm—Werner W. Kleeman

[57] ABSTRACT

An osmotic pump for supplying a fluid medium to a reaction chamber defining a first chamber, for example, for supplying a fluid nutrient to a cell culture located in the reaction chamber, is connected to the reaction chamber by a plurality of channels forming a channel system. The osmotic pump provides a continual supply of fluid medium even under zero gravity conditions. The removal and return of expended reaction medium takes place by means of a channel into a second chamber. This second chamber encloses an operating medium for the osmotic pump such that the chambers form a closed system with the corresponding channels.

8 Claims, 1 Drawing Sheet

APPARATUS FOR SUPPLYING A MEDIUM TO A REACTION CHAMBER

CROSS-REFERENCE TO RELATED APPLICATION

This application is related to the commonly assigned, copending U.S. patent application Ser. No. 06/800,583, filed Nov. 21, 1985, and entitled "CELL CULTURE CHAMBER WITH MEANS FOR AUTOMATIC REPLENISHMENT OF NUTRIENT" now granted as U.S. Pat. No. 4,680,266 on July 14, 1987, the disclosure of which is incorporated herein by reference.

BACKGROUND OF THE INVENTION

The present invention broadly relates to a new and improved apparatus for transfer or infeed of a fluid medium.

In its more particular aspects, the apparatus of the present invention concerns an apparatus or supplying a fluid medium and which comprises at least two chambers. These two chambers are rheologically interconnected or flow communicated with one another by means of a corresponding channel system for the supply and removal of fluid medium.

Cell culturing technology, external to organisms, has been a widespread method in scientific laboratories and in industry. Botanical, zoological or human or homological cells are caused to multiply in a nutrient medium in specially designed apparatuses or vessels which are provided with reaction chambers. After a cell cycle, i.e. after the cell count has doubled, the nutrient medium is normally expended or consumed and must be replaced or replenished with a fresh nutrient medium.

SUMMARY OF THE INVENTION

Therefore, with the foregoing in mind, it is a primary object of the present invention to provide a new and improved apparatus for supplying a fluid medium to a reaction chamber which does not exhibit the drawbacks and shortcomings of the prior art constructions.

Another and more specific object of the present invention aims at providing a new and improved construction of an apparatus of the previously mentioned type which provides a continual supply of fluid medium, for instance cell culture medium or a fluid nutrient, to a reaction chamber or the like.

Another important object of the present invention aims at providing a new and improved construction of an apparatus of the previously mentioned type which also can be used under zero gravity conditions or which can be utilized in different orientations relative to the direction of the force of gravity without requiring substantial assistance of operating personnel.

Yet a further significant object of the present invention aims at providing a new and improved construction of an apparatus of the character described which is relatively simple in construction and design, extremely economical to manufacture, highly reliable in operation, not readily subject to breakdown or malfunction and requires a minimum of maintenance and servicing.

Now in order to implement these and still further objects of the invention, which will become more readily apparent as the description proceeds, the apparatus of the present invention is manifested by the features that an osmotic pump is provided for transfer or supply of a fluid medium such as a cell culture medium or a fluid nutrient to a first chamber of the at least two chambers, which first chamber forms a reaction chamber. At least one other chamber of the at least two chambers defines a second chamber adjacently located to the osmotic pump. This second chamber contains an operating medium for the osmotic pump. The second chamber for the operating medium, the osmotic pump, the reaction chamber and a number of channels of the channel system form a closed system.

In this manner, the medium discharged from the reaction chamber is expelled or returned into the second chamber for the operating medium. In order to allow a sample of the discharged medium to be taken without mixing the discharged medium with the operating medium, a drainage connection between the reaction chamber and the second chamber for the operating medium is advantageously provided by means of a connecting channel possessing a relatively narrow or small cross-section. After opening a cover or seal or the reaction chamber, this connecting channel is accessible for taking the sample, for example, by means of a suction syringe.

The osmotic pump is preferably inserted into a control sleeve or element which is rotatably mounted about its longitudinal axis in the housing of the apparatus in order to block or stop the inflow of the fluid medium to the reaction chamber so that the filled osmotic pump can be inserted into the apparatus before the desired start of the reaction. The second chamber for the operating medium is adjacent to the exterior or outer side of the control sleeve. The control sleeve comprises a connecting channel section in its wall, for example, in its base portion or base wall. This connecting channel section is selectively directable to or alignable with an inlet passage of the reaction chamber or a bypass channel by turning or rotating the control sleeve. At least one further port or opening in the wall of the control housing ensures the connection between the second chamber for the operating medium and the osmotic pump. This port or opening can also be controlled, i.e. obturated, by turning or rotating the control sleeve.

The apparatus according to the invention is especially suitable for conducting experiments, for example, cell-biological experiments, under zero gravity conditions because of the characteristics previously described, since the closed system with automatic fluid medium transfer or exchange avoids the problems of handling liquids under zero gravity conditions. Furthermore, a pressure increase within the closed system is avoided which would be especially disadvantageous for cell cultures during the supply of a nutrient medium.

A suitable filter element is advantageously provided at the outlet passage or outlet of the reaction chamber in order to prevent transport or movement of the solid particles to be treated, for example the cell cultures of biological experiments, and which are enclosed in the reaction chamber, due to the continual flow of fluid medium into the reaction chamber and the resulting discharge from the reaction chamber.

It should be pointed out that the field of application of the apparatus according to the invention is not just limited to space laboratories, but can also include investigations which require a continuous supply of fluid medium and other liquid materials. Examples of such areas of application are, for example, developmental biology and embryology.

Osmotic pumps of a suitable type are known and are commercially available in different specifications in order, for example, to uniformly supply a medication or drug over a long time period upon implantation in test animals.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings there have been generally used the same reference characters to denote the same or analogous components and wherein.

DETAILED DESCRIPTION OF THE PREFERRED EMBODIMENTS

Figure 1:
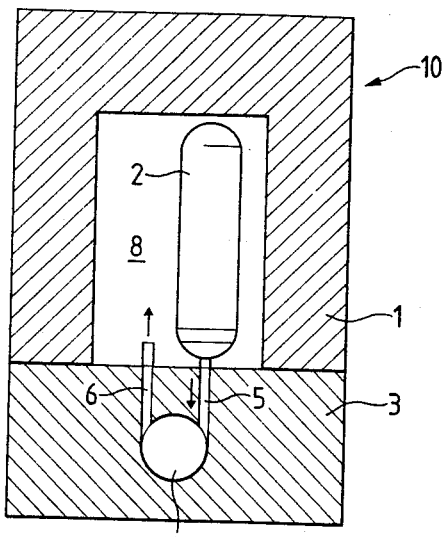
FIG. 1 schematically shows a first exemplary embodiment of an apparatus according to the invention.

Describing now the drawings, it is to be understood that to simplify the showing thereof only enough of the structure of the apparatus for supplying a fluid medium to a reaction chamber has been illustrated therein as is needed to enable one skilled in the art to readily understand the underlying principles and concepts of the present invention. Turning now specifically to FIG. 1 of the drawings, the first embodiment of apparatus 10 illustrated therein by way of example and not limitation, will be seen to comprise a first chamber 4 and a second chamber 8 surrounded or enclosed by a housing 1, 3. The second chamber 8 is connected with the first chamber 4, for example, a reaction chamber, by means of a channel 5 for the transfer or supply of a reaction or fluid medium, such as cell culture medium or a fluid nutrient medium and a channel 6 for the discharge or removal of the expended or discharged medium.

In the apparatus 10, the supply or transfer of the fluid medium into the reaction chamber or first chamber 4 begins immediately subsequent to installing an osmotic pump 2 in the second chamber 8 and filling the second chamber 8 with an operating medium penetrating into the osmotic pump 2. The operating medium may be, for instance, water, a physiological salt solution, the nutrient medium or any other suitable substance appropriate for the intended use. The fluid medium expended or consumed in the reaction chamber or first chamber 4 flows via channel 6 into the second chamber 8 and can mix there with the operating medium for the osmotic pump 2. It is understood that the housing 1, 3 of the apparatus 10 possesses closure ports or separation planes suitable for inserting the osmotic pump 2 and for filling both the first chamber or reaction chamber 4 and the second chamber 8. The design or type or arrangement of these closure ports or separation planes is accommodatable to the respective field of application of the apparatus 10.

Figure 2:
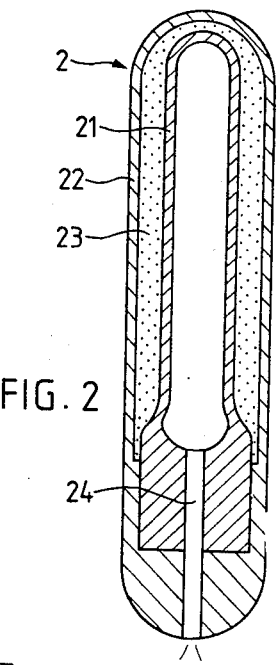
FIG. 2 schematically illustrates a cross-section of an osmotic pump suitable for use in the arrangements of FIGS. 1 and 3.

FIG. 2 illustrates a conventional osmotic pump 2 which comprises an inner storage container or vessel 21 having an impermeable, flexible wall which is pressed inwardly by means of the osmotic pressure in the surrounding semi-permeable outer container or vessel 22 such that the fluid medium to be supplied or transferred to the reaction chamber or first chamber 4 correspondingly flows through a pumping channel 24. Such osmotic pump 2 is, for instance, commercially available from Alza Corp., 950 Page Mill Road, Palo Alto, Calif. and contains an osmotic substance which contains, for instance, a mixture of carbohydrates and salts, which is located in the space or cavity 23 between the outer container or vessel 22 and the inner storage container or vessel 21. This osmotic substance forms molecules of increased size when it combines with the operating medium penetrating through the semi-permeable wall. These larger size molecules can no longer penetrate back through this semi-permeable wall and therefore generate the requisite osmotic pressure in the space or cavity 23. The fluid or reaction medium is correspondingly forced or expelled from the inner storage container or vessel 21 through the pumping channel 24. Such an osmotic pump 2 is illustrated in FIG. 1 in use in the apparatus 10 according to the invention and a further similar osmotic pump 32 is illustrated in FIG. 3 in use in an apparatus 30 according to the invention.

Figure 3:
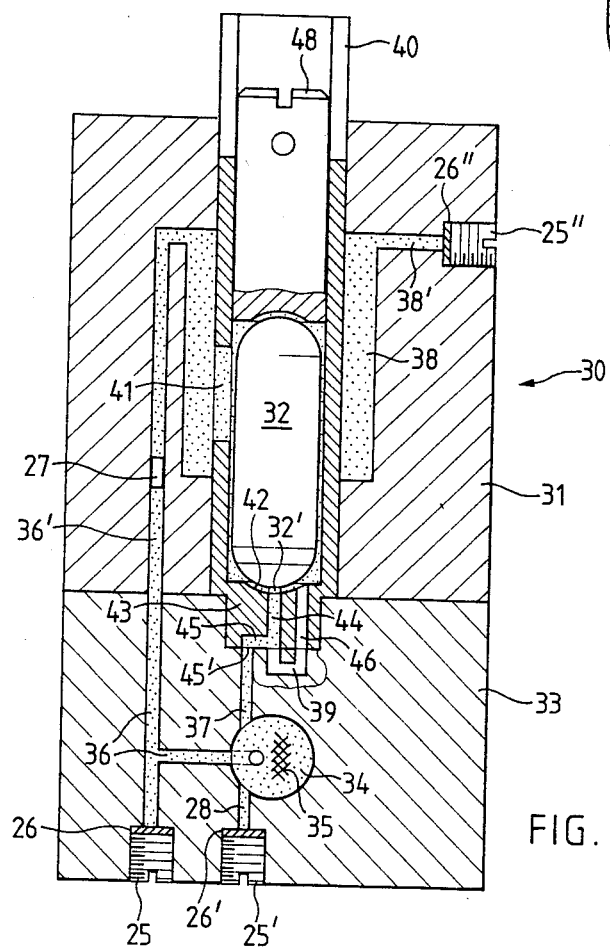
FIG. 3 schematically illustrates a sectional view of a preferred exemplary embodiment of an apparatus according to the invention.

The apparatus 30 according to FIG. 3, in contrast to the apparatus 10 according to FIG. 1, allows for starting or beginning the reaction, i.e. the transfer or supply of the fluid or reaction medium from the osmotic pump 32 to a reaction chamber 34. This starting or beginning of the reaction is accomplished by a simple turning or rotational movement of a control sleeve or element 40 after the filled osmotic pump 32 and the operating medium are already introduced or inserted into the apparatus 30. The osmotic pump 32 is fixedly installed or anchored in the control sleeve 40 such that the osmotic pump 32 is rotatable together with the control sleeve 40 relative to the housing 31, 33 of the apparatus 30. A closure plug 48 or equivalent structure inserted into the control sleeve 40 presses the region of the osmotic pump 32 containing an exit or outlet port or opening 32' against a sealing socket or fitting 42 of the osmotic pump 32 at the base portion or region 43 of the control sleeve 40.

A discharge or outlet passage or channel 44 penetrating through the base portion 43 merges in angled relationship with a junction or branch 45 at its outer region so that a discharge port or opening 45' in the base portion 43 is pivotable by rotating or turning the control sleeve or element 40 through an angle, for example through 90°, selectively to a channel 37 of the reaction chamber 34 or to a bypass channel 39. The fluid or reaction medium travels through the bypass channel 39 while bypassing the reaction chamber 34 and flows through a port or opening 46 substantially directly into a chamber 38.

This chamber 38 is in juxtaposition with the osmotic pump 32 through at least one opening or aperture 41 in the control sleeve or element 40 and contains the operating medium. The cross-section of the bypass channel 39 is shown conveniently displaced by 90° as represented in FIG. 3 so that these two operating positions of the control sleeve 40 are made clear.

An elongated connecting channel or channel section 36 and an upper channel section 36' are provided for discharge of the expended reaction medium from the reaction chamber 34 and lead to the chamber 38 enclosing the operating medium and at least partially surround the control sleeve or element 40. This channel structure 36, 36' preferably has a relatively small diameter or a freely floating separating piston 27 floating in the fluid medium and which is positioned in the upper channel section 36'. Thus any possible mixing between the exhausted or discharged medium expelled from the reaction chamber 34 and the operating medium is confined to a limited region. This permits an analysis of the exhausted or discharged medium by means of suction using a syringe or injection needle or the like, either after opening the reaction chamber 34 by puncturing the same with such needle or after opening a not particularly illustrated closure plug or equivalent structure.

A filling channel 28 which is closed by means of a closure plug 25' discharges or empties into the reaction chamber 34 and is used for filling the reaction chamber 34. This filling channel 28 can also be used for other purposes after removing the closure plug 25' and allows access, for example, after puncturing a seal or membrane 26', which for example may be made of rubber, by means of a not particularly illustrated syringe or injection needle or analogous means, to the reaction chamber 34.

A further closure plug 25" having a seal or membrane 26", which for example may also be made of rubber, permits venting of the chamber 38 by means of a channel 38'. Seals or membranes 26, 26' and 26", which can for example be made of rubber, are placed forwardly of or prior to closure plugs 25, 25' and 25", respectively, which are inserted into the corresponding openings or ports. These seals or membranes 26, 26' and 26" are automatically self-sealing after the withdrawal or removal of the syringe or injection needle or other equivalent means so that no air can enter the closed system.

In order to retain or block solid particles from leaving the reaction chamber 34, a filter element 35, which is schematically illustrated by cross hatching in the reaction chamber 34, is placed prior to or forwardly of the entrance into the channel section 36 i.e. the exit from the reaction chamber 34. The channel 36 is closed at the lower end at the region of the membrane 26 by means of the closure plug 25. The reaction chamber 34 can be provided with at least one not particulary illustrated but conventional glass disc for monitoring the contents of the reaction chamber 34.

All components of the apparatus are advantageously made from a material which can be heated to a suitable sterilization temperature, with the exception of the osmotic pump.

While there are shown and described present preferred embodiments of the invention, it is to be distinctly understood that the invention is not limited thereto, but may be otherwise variously embodied and practiced within the scope of the following claims.

What I claim is:

1. An apparatus for supplying a fluid medium to a reaction chamber, comprising:
    at least two chambers defining a first chamber and a second chamber;
    said first chamber comprising a reaction chamber for receiving a reaction medium;
    an osmotic pump containing the reaction medium and for supplying the reaction medium to said reaction chamber;
    at least one other chamber of said at least two chambers defining said second chamber located adjacent to said osmotic pump and containing an operating medium for operating said osmotic pump;
    a channel system containing a plurality of channels rheologically interconnecting said at least two chambers for supplying the reaction medium from said osmotic pump to said reaction chamber and removing expended reaction medium from said reaction chamber;
    said second chamber, said osmotic pump, said reaction chamber and at least a portion of said channels of said channel system forming a closed system;
    a control sleeve having a longitudinal axis and being mounted for rotation about its longitudinal axis;
    said control sleeve being arranged in flow communication with said osmotic pump;
    said plurality of channels including a channel leading from said control sleeve to said reaction chamber and a bypass channel bypassing said reaction chamber and leading from said control sleeve to said second chamber; and
    said control sleeve, depending upon its rotational position, selectively providing flow communication between said control sleeve and either one of
    (i) said channel leading to said reaction chamber or
    (ii) said bypass channel.

2. The apparatus as defined in claim 1, further including:
    a housing provided for said osmotic pump and said reaction chamber;
    said control sleeve having a base portion and being rotatably mounted in said housing for rotation about said longitudinal axis;
    said osmotic pump being mounted in said control sleeve;
    said control sleeve comprising at least one opening for operatively connecting said second chamber containing said operating medium to said osmotic pump;
    said plurality of channels including an angled discharge channel means located in said base portion of said control sleeve;
    said base portion containing two discharge ports;
    one of said two discharge ports communicating with said channel leading to said reaction chamber and an other one of said two discharge ports communicating with said bypass channel; and
    said angled discharge channel means located in said base portion of said control sleeve, depending upon the rotational position of said control sleeve, selectively providing flow communication between said angled discharge channel means and a desired one of said channel leading to said reaction chamber and said bypass channel.

3. The apparatus as defined in claim 1, wherein:
    said channel system comprises an elongated connecting channel containing said operating medium for operating said osmotic pump and being connected with said reaction chamber and said second chamber; and
    said elongated connecting channel containing means for limiting mixture of said expended reaction medium issuing from said reaction chamber with said operating medium contained within said second chamber.

4. The apparatus as defined in claim 3, wherein:
    said elongated connecting channel comprises an upper channel section; and
    said mixture limiting means constituting a freely floating piston located in said upper channel section for separating said operating medium contained within said second chamber from the expended reaction medium issuing from the reaction chamber.

5. The apparatus as defined in claim 3, further including:

means for rendering accessible said reaction chamber for withdrawing a sample from said reaction chamber.

6. The apparatus as defined in claim 3, further including:
a closure plug closing an end of said elongated connecting channel and which end is remote from said second chamber; and
said elongated connecting channel being accessible through said closure plug for withdrawing a sample of the expended reaction medium contained in said elongated connecting channel.

7. The apparatus as defined in claim 3, wherein:
said reaction chamber comprises an exit means leading to said elongated connecting channel; and
a filter element positioned upstream of said exit means of said reaction chamber.

8. The apparatus as defined in claim 1, wherein:
said reaction chamber is provided with at least one glass disc for monitoring the contents of the reaction chamber.

* * * * *